(12) United States Patent
Boscaro et al.

(10) Patent No.: US 9,908,100 B2
(45) Date of Patent: Mar. 6, 2018

(54) $TIO_2$ MATERIAL THAT IS ABSORBENT IN THE VISIBLE SPECTRUM AND METHOD FOR PRODUCING SAME

(71) Applicants: TOTAL SA, Courbevoie (FR); CENTRE NATIONAL DE LA RECHERCHE SCIENTIFIQUE—CNRS, Paris (FR); ECOLE NATIONALE SUPERIEURE DE CHIMIE DE MONTPELLIER, Montpellier (FR)

(72) Inventors: Paolo Boscaro, Paris (FR); Vasile Hulea, Montpellier (FR); Nathalie Marcotte, Montpellier (FR); François Fajula, Teyran (FR); Anne Galarneau, Montpellier (FR); Francis Luck, Noisy le Grand (FR)

(73) Assignees: TOTAL SA, Courbevoie (FR); Centre National De La Recherche Scientifique—CNRS, Paris (FR); Ecole Nationale Superieure de Chimie de Montpellier, Montpellier (FR)

( * ) Notice: Subject to any disclaimer, the term of this patent is extended or adjusted under 35 U.S.C. 154(b) by 0 days.

(21) Appl. No.: 15/114,757

(22) PCT Filed: Jan. 27, 2015

(86) PCT No.: PCT/FR2015/050187
§ 371 (c)(1),
(2) Date: Jul. 27, 2016

(87) PCT Pub. No.: WO2015/110772
PCT Pub. Date: Jul. 30, 2015

(65) Prior Publication Data
US 2016/0339413 A1    Nov. 24, 2016

(30) Foreign Application Priority Data

Jan. 27, 2014  (FR) ..................................... 14 00194

(51) Int. Cl.
*B01J 21/06*    (2006.01)
*B01J 37/03*    (2006.01)
(Continued)

(52) U.S. Cl.
CPC ............... *B01J 21/063* (2013.01); *A61L 9/18* (2013.01); *B01D 53/007* (2013.01); *B01J 21/18* (2013.01);
(Continued)

(58) Field of Classification Search
CPC ...................................................... B01J 21/063
See application file for complete search history.

(56) References Cited

U.S. PATENT DOCUMENTS

| | | |
|---|---|---|
| 2011/0028311 A1 | 2/2011 | Etacheri et al. |
| 2012/0118723 A1 | 5/2012 | Mau et al. |
| 2012/0165184 A1 | 6/2012 | Lim et al. |

FOREIGN PATENT DOCUMENTS

| | | | |
|---|---|---|---|
| CN | 101462068 A | * | 6/2009 |
| CN | 101462068 A | | 6/2009 |

(Continued)

OTHER PUBLICATIONS

Yu et al, Hydrothermal Preparation and Photocatalytic Activity of Hierarchically Sponge-like Macro-/Mesoporous Titania, 2007, j. phys. chem, vol. 111, pp. 10582-10589.*

(Continued)

*Primary Examiner* — Melvin C Mayes
*Assistant Examiner* — Stefanie Cohen
(74) *Attorney, Agent, or Firm* — Patterson Thuente Pedersen, P.A.

(57) ABSTRACT

The invention relates to a method for the production of a $TiO_2$ material comprising:
 preliminary mixing a titanium alkoxide with an acid;
 adding water, a phase separator and of an N source to the mixture thereby obtaining a $TiO_2$ gel;
(Continued)

washing the TiO$_2$ gel with isopropanol;

drying and calcining the TiO$_2$ gel to produce the material. The invention also relates to a TiO$_2$ material exhibiting an absorbance in the visible spectrum and in particular a light absorption at 500 nm which is greater than 50% of the light absorption at 400 nm, and its use as photocatalyst for the degradation of pollutants in air or water and water splitting into H$_2$, under radiation in the visible spectrum.

7 Claims, 4 Drawing Sheets

(51) Int. Cl.

| | | |
|---|---|---|
| A61L 9/18 | (2006.01) | |
| B01J 35/00 | (2006.01) | |
| C01B 3/04 | (2006.01) | |
| C02F 1/32 | (2006.01) | |
| B01J 27/24 | (2006.01) | |
| B01D 53/00 | (2006.01) | |
| B01J 21/18 | (2006.01) | |
| B01J 35/04 | (2006.01) | |
| B01J 35/06 | (2006.01) | |
| B01J 37/04 | (2006.01) | |
| B01J 37/06 | (2006.01) | |
| B01J 37/08 | (2006.01) | |
| C01B 13/02 | (2006.01) | |
| C02F 1/72 | (2006.01) | |
| B01J 35/02 | (2006.01) | |
| B01J 35/10 | (2006.01) | |
| B01J 27/20 | (2006.01) | |

(52) U.S. Cl.
CPC .............. *B01J 27/24* (2013.01); *B01J 35/004* (2013.01); *B01J 35/04* (2013.01); *B01J 35/06* (2013.01); *B01J 37/033* (2013.01); *B01J 37/036* (2013.01); *B01J 37/04* (2013.01); *B01J 37/06* (2013.01); *B01J 37/08* (2013.01); *C01B 3/042* (2013.01); *C01B 13/0207* (2013.01); *C02F 1/32* (2013.01); *C02F 1/725* (2013.01); *B01D 2255/20707* (2013.01); *B01D 2255/802* (2013.01); *B01D 2258/06* (2013.01); *B01D 2259/802* (2013.01); *B01J 27/20* (2013.01); *B01J 35/023* (2013.01); *B01J 35/026* (2013.01); *B01J 35/1033* (2013.01); *B01J 35/1061* (2013.01); *B01J 35/1076* (2013.01); *C02F 2305/10* (2013.01); *Y02E 60/364* (2013.01); *Y02W 10/37* (2015.05)

(56) References Cited

FOREIGN PATENT DOCUMENTS

| CN | 101721985 A | * | 6/2010 |
|---|---|---|---|
| CN | 101721985 A | | 6/2010 |
| CN | 102451671 A | | 5/2012 |

OTHER PUBLICATIONS

English translation of CN101462068, 2009.*
English translation fo CN101721985, 2010.*
English translation of International Search Report for PCT/FR2014/053483, dated Jun. 30, 2015, 3 pages.
Senthelhathan J et al: "Photodegradation of methyl parathion and dichlorvos from drinking water with H-doped TiOunder solar radiation", Chemical Engineering Journal, Elsevier Sequoia, Lausanne, CH, vol. 172, No. 2, Jun. 15, 2011 (Jun. 15, 2011), pp. 678-688, XP028270639, ISSN: 1385-8947, DOI: 10.1016/J.CEJ.2011.06.035 [retrieved on Jun. 22, 2011].
Chen et al. "Plasmonic Photocatalyst for H$_2$ Evolution in Photocatalytic Water Splitting". J. Phys. Chem. C(2011), 115, pp. 210-216.
Mohamed, et al. "Preparation and characterization of nano-silver/mesoporous titania photocatalysts for herbicide degradation". Microporous and Mesoporous Materials 142 (2011) pp. 130-138.
Sakthivel, et al. "Enhancement of photocatalytic activity by metal deposition: characterization and photonic efficiency of Pt, Au and Pd deposited on TiO$_2$ catalyst", Water Research 38 (2004) pp. 3001-3008.
Silva et al. "Influence of Excitation Wavelength (UV or Visible Light) on the Photocatalytic Activity of Titania Containing Gold Nanoparticles for the Generation of Hydrogen or Oxygen from Water". JACS Articles, published Dec. 13, 2010, 9 pgs.
Šojić, et al. "Photocatalytic degradation of selected herbicides in aqueous suspensions of doped titania under visible light irradiation". Journal of Hazardous Materials 179 (2010), pp. 49-56.

\* cited by examiner

TIO₂ MATERIAL THAT IS ABSORBENT IN THE VISIBLE SPECTRUM AND METHOD FOR PRODUCING SAME

RELATED APPLICATIONS

The present application is a National Phase entry of PCT Application No. PCT/FR2015/050187, filed Jan. 27, 2015, which claims priority from FR Patent Application No. 14/00194, filed Jan. 27, 2014, said applications being hereby incorporated by reference herein in their entirety.

FIELD OF THE INVENTION

The technical field in which the invention particularly lies is that of materials usable as photocatalysts activated by radiation in the visible spectrum and more particularly that of titanium oxide ($TiO_2$) materials which can be used as photocatalysts activated by radiation in the visible spectrum, in particular for degradation of pollutants in air and water or for water splitting, and their manufacturing processes.

BACKGROUND OF THE INVENTION

The state of the art currently shows that obtaining a high conversion degree (i.e. the ratio of the amount of transformed reactant to the total amount of reactant present in a given volume and at a given time) requires the development of nanostructured materials operating as catalyst with a well-defined and controlled composition as well as a specific shape.

As regards $TiO_2$ photocatalysts, mention may be made, among the best obtainable results, of catalysts comprising $TiO_2$ nanotubes which are grown on titanium sheets. These photocatalysts are activated by radiation exclusively in the visible spectrum.

Although these photocatalysts are very efficient in gas phase, their use in liquid phase cannot be contemplated because of the instability of the nanotubes deposited on the sheets.

Other $TiO_2$ photocatalysts have been studied. In particular, Degussa P25 $TiO_2$ acts as a reference $TiO_2$ photocatalyst. This photocatalyst proves to be effective under UV radiation. However, its ability to absorb light is not satisfactory.

In order to improve the ability of $TiO_2$ photocatalysts to absorb light, particles of noble metals, such as platinum, palladium, gold and silver, have been added.

Documents "Influence of Excitation Wavelength (UV or Visible Light) on the Photocatalytic Activity of Titania Containing Gold Nanoparticles for the Generation of Hydrogen or Oxygen from Water", G. C. Silva et al., J. Am. Chem. Soc., 2011, 113, pp 595-602, and "Plasmonic Photocatalyst for H2 Evolution in Photocatalytic Water Splitting", J. J. Chen et al., J. Phys. Chem. C, 2011, pages 115-210, describe methods for synthesizing mesoporous $TiO_2$/gold photocatalysts for water splitting. These materials are nanometric and are composed of particles of "P25" $TiO_2$ with a diameter of 20 nm to 30 nm with gold particles with a diameter of 2 nm to 4 nm.

Absorption of these materials is intense in the UV region, in particular 300 nm, but is zero at 400 nm and extremely low between 500 nm and 600 nm.

Document "Enhancement of photocatalytic activity by metal deposition: characterisation and photonic efficiency of Pt, Au and Pd deposited on $TiO_2$ catalyst", S. Sakthivel et al., Water Research, 2004, 38, pages 3001-3008, describes a method for synthesizing a $TiO_2$ photocatalyst exhibiting platinum, gold or palladium deposited at its surface for degrading organic dyes, in particular Acid Green 16, under UV radiation. This material exhibits a greater absorption at 500 nm than 400 nm.

Papers "Preparation and characterisation of nano-silver/mesoporous titania photocatalysts for herbicide degradation", M. M. Mohamed et al., Microporous and Mesoporous Materials, 142 (2011), pages 130 to 138, and "Photocatalytic degradation of selected herbicides in aqueous suspensions of doped titania under visible light irradiation", D. V. Sojic et al., J. Harzardous Materials, 179 (2010), pages 49 to 56, describe the synthesis of $TiO_2$ materials for the degradation of herbicides in water. These materials moreover also comprise silver, iron or nitrogen. The $TiO_2$/silver material is synthesized from polyoxyethylene lauryl ether (POL), $AgNO_3$ and $Ti(OiPr)_4$ and is provided in the form of nanoparticles with a diameter of between 15 and 25 nm. The absorption in visible light is not given for this material. The $TiO_2$/Fe material is synthesized from $FeCl_3$ (iron(III) trichloride) and $TiCl_4$ (titanium tetrachloride). It is provided in the form of nanoparticles with a diameter of between 5 and 7 nm. The reflectance of this material is virtually 100% at 500 nm, corresponding to an F(R) (Kubelka-Munk) absorbance of 0. The $TiO_2$/nitrogen material is synthesized from $Ti(OH)_4$ (titanium tetrahydroxide) and urea. It is provided in the form of nanoparticles with a diameter of between 6 and 8 nm and its reflectance at 400 nm is approximately 40%, corresponding to an F(R) (Kubelka-Munk) absorbance of 0.44, whereas at 500 nm it is approximately 90%, corresponding to an F(R) (Kubelka-Munk) absorbance of 0.005, i.e. a light absorbance at 500 nm of 1% of the light absorption at 400 nm.

Paper "Photocatalytic degradation of lindane under UV and visible light using N-doped $TiO_2$", J. Senthilnathan et al., Chem. Eng. J., 161 (2010), pages 83 to 92, describes the synthesis of a $TiO_2$ material doped with nitrogen for the degradation of a pesticide. This material is obtained from $Ti(OiPr)_4$ in EtOH and $N(CH_2CH_3)_3$ (triethylamine) in acid environment. It is provided in the form of nanoparticles with a size between 29 and 71 nm.

Document CN102744059 describes a method for synthesising a mesoporous photocatalyst made of $TiO_2$ and silver for decontaminating lake water, seawater, sewage and industrial wastewater.

Thus, some of these photocatalysts require the use of noble metal nanoparticles and are consequently more expensive.

Furthermore, the majority of these photocatalysts may be difficult to synthesize. In addition, they are subject to Ostwald ripening, a phenomenon in which the nanoparticles aggregate together causing their gradual deactivation; consequently, the nanoparticles are not thermally very stable. Furthermore, the $TiO_2$ nanoparticles suspended in a solution are difficult to separate from this solution.

Thus, a $TiO_2$ material exhibiting an absorbance in the visible spectrum, the manufacture of which is relatively inexpensive and the handling of which is easy, still constitutes a need which is currently not yet satisfied.

SUMMARY OF THE INVENTION

Thus, here one objective is in particular to provide a method which makes it possible to manufacture a material which overcomes the drawbacks of the prior art presented above.

To this aim, a method for the production of a $TiO_2$ material is provided. This method comprises:

preliminary mixing a titanium alkoxide with an acid;
adding water, a phase separator and an N source to the mixture of titanium alkoxide and acid, thereby obtaining a $TiO_2$ gel;
washing the $TiO_2$ gel with isopropanol (iPrOH);
drying and calcining the $TiO_2$ gel to produce the $TiO_2$ material exhibiting mesoporosity and/or macroporosity and comprising at least 60 wt. %, preferably at least 70 wt. %, $TiO_2$ in the form of anatase and elemental carbon and/or elemental nitrogen in trace amount, the percentages being calculated with respect to the total weight of the material.

Such a method has the not insignificant advantage of making it possible to manufacture a $TiO_2$ material exhibiting an absorbance in the visible spectrum so that the light absorption at 500 nm is greater than 50% of the light absorption at 400 nm.

The titanium alkoxide is preferably $Ti(OiPr)_4$.

The titanium alkoxide:acid molar ratio is preferably between 1:1 and 1:0.5.

The acid may be HCl.

The titanium alkoxide:units of EO monomer in the phase separator molar ratio may be between 1:0.6 and 1:0.2.

The phase separator is advantageously poly(ethylene oxide) (PEO), preferably at a number average molar mass (Mn) of higher than or equal to 10 000.

The titanium alkoxide:N source molar ratio may be between 1:1 and 1:0.75.

The N source is preferably N-methylformamide (NFA).

A $TiO_2$ material is also provided, which exhibits mesoporosity and/or macroporosity and comprises at least 60 wt. %, preferably at least 70 wt. %, $TiO_2$ in the anatase form and elemental carbon and/or elemental nitrogen in trace amount, the percentages being calculated with respect to the total weight of the material,
and exhibiting an absorbance in the visible spectrum; and
the light absorbance at 500 nm of which is greater than 50%, preferably greater than 60%, of the light absorption at 400 nm.

Such a material has the advantage of being activatable by solar energy. Thus, supplying a artificial UV radiation source is no longer necessary; exposure to solar radiation is sufficient. The activation of this material is thus economical and comprises few environmental disadvantages.

The $TiO_2$ of this material may be in the form of a monolith, in particular of a monolithic film.

The material is advantageously devoid of additive other than C and N.

It may in particular be obtained by the above method.

Also provided is the use of the material described above as photocatalyst for the degradation of pollutants in air or in water under radiation in the visible spectrum. Another use of such a material as photocatalyst is water splitting to produce $H_2$ and $O_2$.

Thus, decontamination in air or in water is carried out with solar energy as energy supply or at least main energy supply. There is the same advantage for water splitting into $H_2$ and $O_2$.

BRIEF DESCRIPTION OF THE DRAWINGS

Other objectives, features and advantages will become apparent from the description given below by way of illustration and without limitation, with reference to the drawings, among which.

DETAILED DESCRIPTION OF THE DRAWINGS

Figure 1:
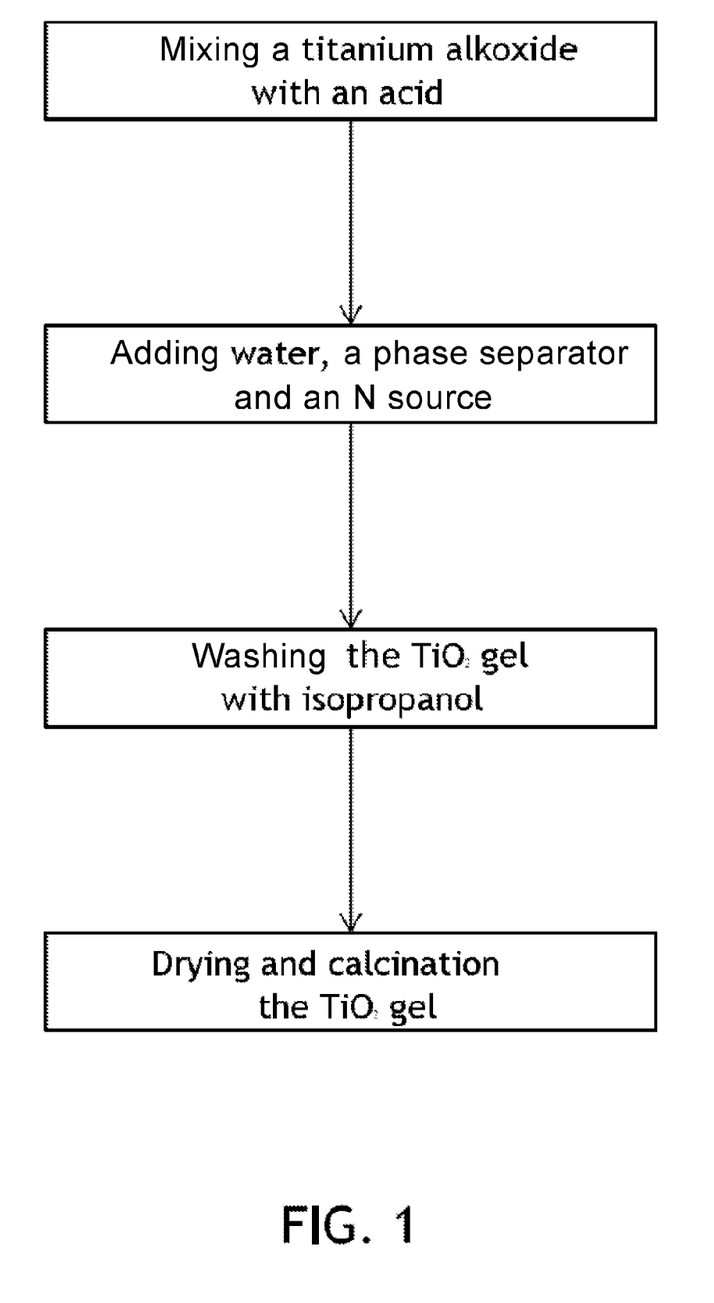
FIG. 1 is a diagram illustrating the steps of the method for the production of a $TiO_2$ material according to the invention.

With reference to FIG. 1, a method for the manufacture of a $TiO_2$ material exhibiting mesoporosity and/or macroporosity and comprising at least 60 wt. %, preferably at least 70 wt. %, $TiO_2$ in the anatase form and elemental carbon (C) and/or elemental nitrogen (N) in trace amount, the percentages being calculated with respect to the total weight of the material, is described below.

The amount of elemental C and elemental N is determined by chemical analysis according to the method described below in the "Methods" part.

Throughout the present disclosure, anatase refers to a tetragonal titanium oxide ($TiO_2$), exhibiting an $I4_1/amd$ space group, having the unit cell parameters: a=3.7852 Å (angstrom); c=9.5139 Å, and with a theoretical density of 3.893. These figures can slightly vary by ±0.05 Å (for a and c) and by ±0.1 (for density).

The method comprises:
preliminary mixing a titanium alkoxide with an acid;
adding water, a phase separator and an N source to the preliminary mixture thereby obtaining a $TiO_2$ gel;
washing the $TiO_2$ gel with isopropanol (iPrOH);
drying and calcining the gel, thereby producing the $TiO_2$ material.

The $TiO_2$ material is never present in the form of a nanoparticles suspension throughout the whole of the manufacturing method.

Preliminary mixing of the titanium alkoxide with an acid means that these two compounds are brought into the presence of one another before mixing them with other compounds used in the method.

Preliminary mixing may be carried out in an ice bath at approximately 0° C. and while stirring. Stirring the mixture is advantageously progressive: the titanium alkoxide is first of all placed at 0° C. under slow stirring, in particular in order to ensure that the magnetic bar does not get stuck in the titanium alkoxide. As the acid is added to the titanium alkoxide, the mixture becomes fuming and less viscous; the stirring rate is then increased up to a value of between approximately 300 rev/min and approximately 400 rev/min, preferably between approximately 300 rev/min and approximately 350 rev/min. Above 400 rev/min, there is a risk of the magnetic bar getting stuck in the mixture.

Titanium alkoxide refers to a compound of general formula $Ti(OR_1)(OR_2)(OR_3)(OR_4)$, wherein each of the $R_1$ to $R_4$ groups is, independently of the others, a branched carbon chain comprising between 3 and 8 carbon atoms, preferably between 3 and 5 carbon atoms.

The branched carbon chains comprising between 3 and 5 carbon atoms are chosen from the group consisting of: $—CH(CH_3)_2$ (isopropyl); $—CH(CH_3)—CH_2—CH_3$ (sec-butyl): $—CH_2—CH(CH_3)_2$ (isobutyl); $—CH(CH_3)_3$ (tert-butyl); $—CH(CH_3)—CH_2—CH_2—CH_3$ (1-methylbutyl); $—CH(CH_3)—CH(CH_3)_2$ (1,2-dimethylpropyl); $—CH_2—CH(CH_3)—CH_2—CH_3$ (2-methylbutyl); $—CH_2—C(CH_3)_3$ (2,2-dimethylpropyl); $—(CH_2)_2—CH(CH_3)_2$ (3-methylbutyl); $—CH(CH_2—CH_3)_2$ (1-ethylpropyl); and $—C(CH_3)_2—CH_2—CH_3$ (1,1-dimethylpropyl).

Advantageously, $R_1$ to $R_4$ are the same carbon chain comprising between 3 and 5 carbon atoms. Thus, the titanium alkoxide can be chosen from the group consisting of: $Ti(OiPr)_4$ (titanium tetra(isopropoxide)); $Ti(Osec-Bu)_4$ (titanium tetra(sec-butoxide)): $Ti(OiBu)_4$ (titanium tetra(isobutoxide)); $Ti(Otert-Bu)_4$ (titanium tetra(tert-butoxide)); $Ti(OCH(CH_3)—CH_2—CH_2—CH_3)_4$ (titanium tetra(1-methylbutanolate)); $Ti(OCH(CH_3)—CH(CH_3)_2)_4$ (titanium tetra(1,2-methylpropanolate)); $Ti(OCH_2—CH(CH_3)—CH_2—CH_3)_4$ (titanium tetra(2-methylbutanolate)); $Ti(OCH_2—C(CH_3)_3)_4$ (titanium tetra(2-dimethylpropanolate)); $Ti(O(CH_2)_2—CH(CH_3)_2)_4$ (titanium tetra(3-methylbutanolate)); $Ti(OCH(CH_2—CH_3)_2)_4$ (titanium tetra(1-ethylpropanolate)); and $Ti(OC(CH_3)_2—CH_2—CH_3)_4$ (titanium tetra(1,1-dimethylpropanolate)).

Preferably, the branched carbon chain is iPr (isopropyl: $—CH(CH_3)_2$). Thus, the titanium alkoxide preferably exhibits the following formula: $Ti(OiPr)_4$.

The acid refers to a proton-donating compound. The titanium alkoxide:acid molar ratio is advantageously between 1:1 and 1:0.5. The acid may be chosen from the group consisting of: HCl (hydrochloric acid), $HNO_3$ (nitric acid), $H_2SO_4$ (sulfuric acid) and $CH_3COOH$ (acetic acid).

Preferably, the acid is HCl. In the latter case and if the titanium alkoxide is $Ti(OiPr)_4$, the $Ti(OiPr)_4$:HCl molar ratio is advantageously between 1:1 and 1:0.5.

The phase separator refers to a compound which, as the $TiO_2$ is formed, comes in between the $TiO_2$ and water, thereby making it possible to obtain a macroporous structure after it is removed. Generally, the separator is a PEO polymer or a copolymer comprising at least one PEO (poly(ethylene oxide)) block. Among the PEO polymers, PEOs with a number average molar mass of approximately 10 000 and of approximately 20 000 are preferred. Among the diblock copolymers, mention may be made of PEOnPPOm (copolymer comprising a first block with n ethylene oxide units and a second block with m propylene oxide units). Among the triblock copolymers, mention may be made of PEOnPPOmPEOn (copolymer comprising a first block with n ethylene oxide units, a second block with m propylene oxide units and a third block with n ethylene oxide units).

The titanium alkoxide:phase separator:water ratio determines the macropore homogeneity within the $TiO_2$ material. Advantageously, the titanium alkoxide:EO (EO monomer units in the separator) molar ratio is between 1:0.6 and 1:0.2. The titanium alkoxide:$H_2O$ molar ratio is between 1:3 and 1:15.

In the case where the titanium alkoxide is $Ti(OiPr)_4$, the $Ti(OiPr)_4$:EO molar ratio is preferably between 1:0.6 and 1:0.2. The $Ti(OiPr)_4$:$H_2O$ molar ratio is preferably between 1:3 and 1:15.

The N (nitrogen) source is a compound capable of releasing at least one N atom. Advantageously, the titanium alkoxide:N source molar ratio is between 1:1 and 1:0.75.

The N source is preferably urea, $NH_4NO_3$ (ammonium nitrate) or NFA (N-methylformamide). Preferably, the N source is NFA. In the latter case and if the titanium alkoxide is $Ti(OiPr)_4$, the $Ti(OiPr)_4$:NFA molar ratio is between 1:1 and 1:0.75.

In a specific embodiment, an alcohol can be added at the same time as the phase separator, the water and the N source. Preferably, this alcohol is EtOH (ethanol). In this case, the $Ti(OiPr)_4$:EtOH molar ratio is advantageously between 1:1.5 and 1:1.

Gelation of the $TiO_2$ is obtained, for example, after exposure to a temperature of between approximately 20° C. and approximately 80° C., preferably between approximately 30° C. and approximately 60° C., preferably again at approximately 40° C., until the $TiO_2$ has completely gelled.

After complete gelation, the $TiO_2$ gel is left for ripening at a temperature of between approximately 40° C. and approximately 80° C., preferably between approximately 50° C. and approximately 70° C., preferably again at approximately 60° C. The $TiO_2$ gel is ripen for a period of time of between approximately 10 h and approximately 40 h, preferably between 15 h and approximately 30 h, preferably again approximately 24 h.

Calcination of the dried $TiO_2$ gel is advantageously carried out between 250° C. and 600° C., preferably between 300° C. and 500° C., more preferably still between 325° C. and 375° C., for a period of time of between 2 h and 12 h, preferably between 4 h and 6 h, more preferably still of between 4 h 30 and 5 h 30. For example, calcination of the $TiO_2$ gel is carried out at approximately 350° C. for approximately 5 hours, with a rise in temperature at 0.5° C./min.

After calcination, the solid is cooled at ambient temperature.

Alternatively, a second calcination may be carried out after the cooling under the same conditions as the first calcination.

Material

A $TiO_2$ material is described below. This material may be obtained from the method described above.

This material exhibits mesoporosity and/or macroporosity and comprises at least 60 wt. %, preferably at least 70 wt. %, $TiO_2$ in the anatase form and elemental carbon and elemental nitrogen in trace amount, the percentages being calculated with respect to the total weight of the material. It exhibits an absorbance in the visible spectrum and in particular the light absorption at 500 nm is greater than 50%, preferably greater than 60%, of the light absorption at 400 nm.

The "visible spectrum", also known as "optical spectrum", refers to the part of the electromagnetic spectrum which is visible to the human eye and commonly between approximately 400 nm and approximately 800 nm. It corresponds to what is also known as "light", which refers to all of the electromagnetic waves visible by the human eye. The terms of "visible spectrum", "optical spectrum" or "light" are taken throughout the whole of the present disclosure as being synonyms. The use of one term or another in the present disclosure will thus be understood as a simple variation in verbal formulation and not as determining any distinction.

The amount of elemental C and/or elemental N trace is determined by chemical analysis according to the method described below.

The elemental C and the elemental N are present in trace amount, i.e. the amount of each is less than or equal to approximately 2 wt. %, preferably less than or equal to approximately 1.5 wt. %, preferably again less than or equal to approximately 1 wt. %, with respect to the total weight of the material. Advantageously, the total amount of N and C is preferably less than 2.5 wt. %.

The $TiO_2$ is in the form of objects exhibiting at least micrometric dimensions, i.e. at least two of the dimensions of these objects are equal to or greater than 1 am. Thus, this $TiO_2$ is easier to handle in comparison with the $TiO_2$ nanoparticles of the prior art and can be easily separated from solutions to which it has been added, for example by sedimentation.

When none of the dimensions of the objects is greater than or equal to 5 mm, the $TiO_2$ is present in the powder form. The powder can be compacted into tablets in order to form even larger objects.

When these objects exhibit at least one dimension greater than or equal to 5 mm, the term used will then be monoliths. The material in the form of monoliths, in particular when the three dimensions are greater than 3 mm, preferably at least one dimension greater than 1 cm, is even easier to handle.

The monoliths making up the material can have the shape of rods, hollow cylinders, sheets, and the like. In particular, when they have the shape of hollow cylinders or sheets, they can be present alone or attached to a support.

Whether it is in the powder or monolith form, the material preferably exhibits open macropores and mesopores. The mesoporous volume of the material is advantageously greater than approximately 0.1 $cm^3/g$, preferably greater than approximately 0.2 $cm^3/g$, more preferably still greater than approximately 0.23 $cm^3/g$. It can exhibit mesopores with a diameter of between approximately 2 nm and approximately 10 nm, preferably between approximately 3 nm and approximately 8 nm, more preferably still between approximately 4 nm and approximately 5 nm.

The macroporous volume of the material is advantageously greater than approximately 0.3 $cm^3/g$, preferably greater than approximately 0.5 $cm^3/g$, more preferably still greater than approximately 0.7 $cm^3/g$. It can exhibit macropores with a diameter of between approximately 2 μm and approximately 10 μm, preferably between approximately 3 μm and approximately 8 μm, more preferably still between approximately 4 μm and approximately 5 μm.

Generally, the macroporosity of the material makes the passage of a fluid through the latter possible by exerting a low pressure differential, i.e. of less than approximately 10 bar, preferably of less than approximately 7 bar, more preferably still between approximately 1 bar and approximately 5 bar, in order to be able to use this material for continuous catalytic treatments.

Furthermore, these macroporosity and mesoporosity characteristics make it possible to avoid a pressure drop when a pressure differential is applied.

The material is devoid of metals, which makes the synthesis simpler since there is no need to add any metal additive, thus eliminating the need to provide for the reduction of metals before they are used. Thus, the material is more economical.

The material can be used as photocatalyst for the degradation of pollutants in air or water under radiation in the visible spectrum.

It can also be used as photocatalyst for water splitting into $H_2$ (hydrogen) under radiation in the visible spectrum.

Methods

XRD (X-Ray Diffraction) Measurement

The XRD measurement of the materials is carried out with a Bruker D8 Advance device using the Kα line of copper with λ=1.5405 Å, 2θ of 4° to 70°, per pitch of 0.02°.

Absorption Spectrum Measurement

The diffuse reflectance (DRUV) spectra of the solid samples are measured with a PerkinElmer Lambda-35 spectrophotometer equipped with an integrating sphere (Labsphère) using $BaSO_4$ as reference. The DRUV spectra are subsequently converted into Kubelka-Munk (F(R)) units in order to obtain the absorption spectra.

Chemical Analysis for the Determination of the Amount of N, of C and of H

The analyses of the elements (N, C, H) were carried out by combustion on a Fisons EA1108 device.

Degradation Test on Orange G Dye 20 ml of aqueous solution of Orange G dye are placed in a 50 ml reactor (made of quartz or glass). The solution is acidified with HCl down to a pH of less than 5. The Orange G dye is introduced into the reactor in an amount sufficient to reach the concentration of 80 mg/l. 150 mg of the analyzed material are introduced into the reactor (except for the control sample).

The reactor is subsequently placed under a Ne (neon) lamp in order to illuminate the material under visible light during 1 h 30. Some of the materials can be placed in darkness for the same time for comparison.

The supernatant is analyzed by UV-visible spectrometry in a cell with a length of 1 cm (optical path) with a Perkin-Elmer Lambda-40 (double beam) spectrophotometer, with an aqueous HCl solution as reference. The results are analyzed within a wavelength range of between 250 and 700 nm.

Degradation Test on Orange 7 Dye Under Solar Radiation 50 ml of an aqueous solution having a Acid Orange 7 dye (also known under the name of Orange II dye: obtained from Sigma-Aldrich under the name AO7 sodium salt, BioXtra, dye content >85%, $10^{-4}$ M) concentration of $10^{-4}$ mol/l are prepared and acidified to pH 3.

12.5 mg of material are placed in the aqueous solution and the combined mixture is exposed to solar radiation or stored in darkness under stirring. Samples of 4 ml of the solution are regularly taken and centrifuged at 5000 rev/min during 10 min.

The supernatant is analyzed by UV-visible spectrometry in a cell with a length of 1 cm (optical path) with a Shimadzu UV-2450 spectrophotometer, with an aqueous HCl solution as reference. The results are analyzed at a wavelength of 484 nm corresponding to the maximum absorption of Orange II dye.

Examples

The amounts of the products, expressed as molar ratios with respect to the amount of titanium alkoxide, are presented in table 1 below, "x" then means x mol per 1 mole of titanium alkoxide.

TABLE 1

|  | Example 1 | Example 2 | Example 3 | Example 4 |
|---|---|---|---|---|
| Ti(OiPr)$_4$ | 1 | 1 | 1 | 1 |
| PEO | 0.57 | 0.56 | 0.56 | 0.57 |
| H$_2$O | 10.05 | 7.58 | 7.66 | 6.90 |
| HCl | 0.65 | 0.89 | 0.91 | 0.64 |
| NFA | 0.933 | 0.905 | 0.906 | 0.933 |
| EtOH | 0 | 0 | 0 | 1.23 |

Ti(OiPr)$_4$ is mixed beforehand with HCl in a reactor in order to acidify it. Water, the PEO (Mn=10 000, except for example 3, where Mn=20 000), the NFA (N-methylformamide) and optionally the EtOH (ethanol) are placed on ice before being added to the mixture. The combination is mixed while the reactor is immersed in an ice bath for 4 min. The reactor is subsequently hermetically closed and exposed to 40° C. for gelation. After complete gelation, the obtained TiO$_2$ gel is left at 60° C. for 24 hours for ripening. The TiO$_2$ gel is subsequently washed with iPrOH (isopropanol) and dried by evaporation at 40° C. for one week. The dry TiO$_2$ gel is pretreated in an oven at 40° C. and afterwards calcined at 350° C. for 5 hours.

A fifth example, corresponding to example 2 but having been subjected to a second calcination under the same conditions as the first calcination, was tested.

Figure 2:
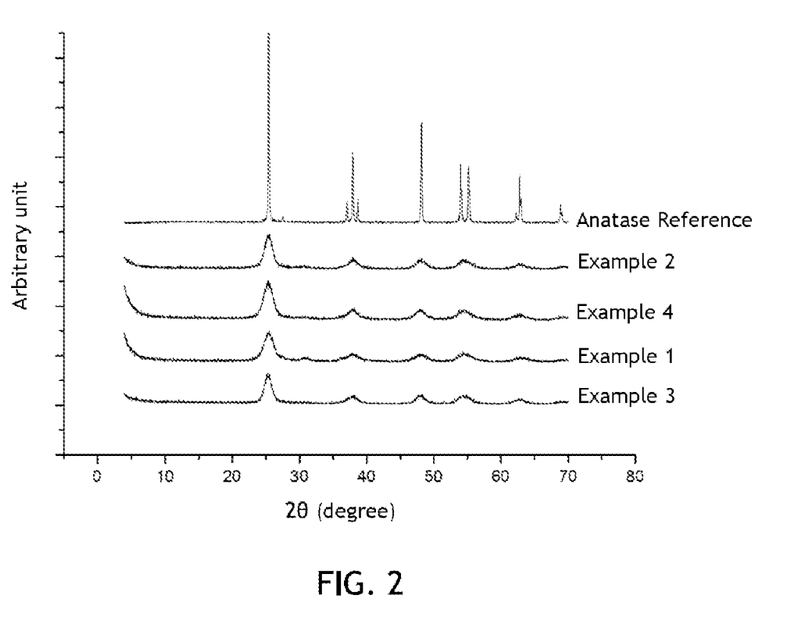
FIG. 2 is a graph showing the XRD measurements for the materials of examples 1 to 4, and also for the reference $TiO_2$ (anatase, Aldrich), in arbitrary units as a function of the 28 angle for values of the latter of between 5° and 70°.

FIG. 2 shows the XRD measurements for examples 1 to 4 with respect to a reference anatase which is TiO$_2$ (anatase, Aldrich) (sold under the reference 248576, −325 mesh, purity >99%, by Sigma-Aldrich). It is thus observed that the material obtained is indeed anatase for these examples.

Examples 1, 2 and 5 give materials in the form of monoliths and powder, example 3 gives a material in the powder form and example 4 gives a material in the form of monoliths.

Figure 3:
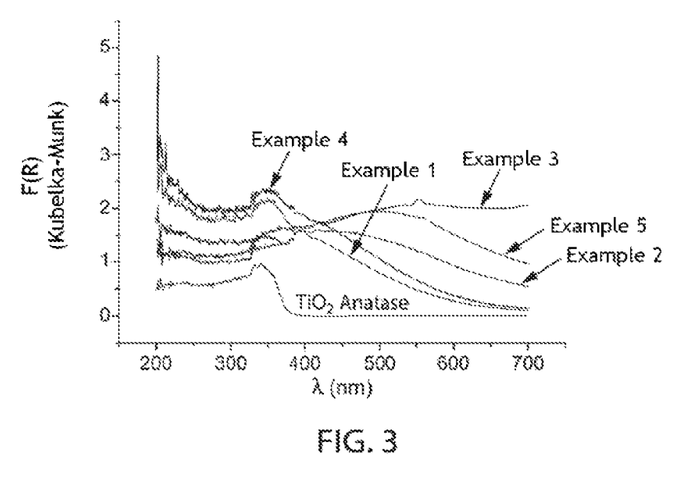
FIG. 3 is a graph showing the absorbance of the materials of examples 1 to 5 and that of the reference $TiO_2$ (anatase), in Kubelka-Munk units, as a function of the wavelength for values of the latter of between 200 nm and 700 nm.

The F(R) (Kubelka-Munk) absorbance of examples 1 to 5 is measured between 200 nm and 700 nm and is represented in FIG. 3. It is observed, from the curves represented in FIG. 3, that the materials of examples 1 to 5 absorb in wavelengths over 400 nm, contrary to the anatase material from Aldrich. The ratios ($A_{500nm}/A_{400nm}$) of the absorbance at 500 nm to the absorbance at 400 nm of the materials of examples 1 to 5 are given in the following table 2.

TABLE 2

|  | Example 1 | Example 2 | Example 3 | Example 4 | Example 5 |
|---|---|---|---|---|---|
| $A_{500\,nm}/A_{400\,nm}$ | 51.5% | 91.3% | 119% | 56.7% | 120% |

The degradation test on Orange G dye was carried out for three of the materials. For example 4, the test was carried out under a lamp and in darkness, which makes it possible to conclude that the degradation of Orange G dye is indeed due to the presence of the material.

Figure 4:
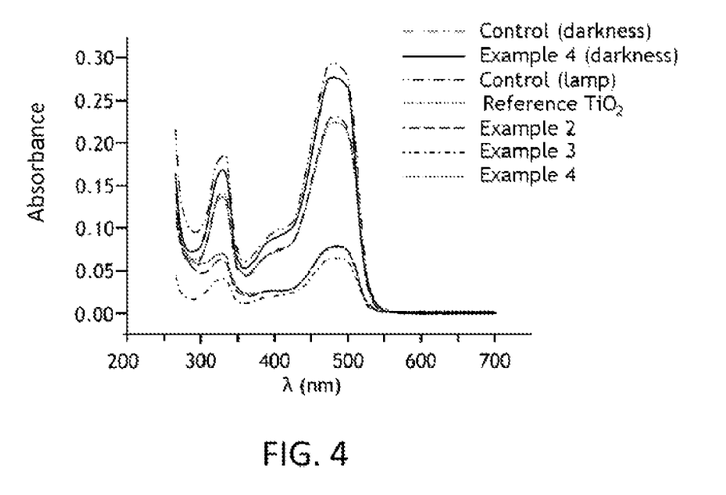
FIG. 4 is a graph showing the absorbance of solutions containing an Orange G dye into which the materials of examples 2 to 4 and reference $TiO_2$ (anatase, Aldrich) have been added, after exposure to light for 1 h 30, as a function of the wavelength for values of the latter of between 250 nm and 700 nm.

FIG. 4 shows the absorbance of the solution after exposure to light for 1 h 30. The ratios (A/A$_{ref}$) of the absorbance at 500 nm of the solutions which have contained the materials of examples 2 to 4 to the absorbance at 500 nm of the control sample (that is to say, without photocatalyst) exposed to the light are presented in table 3.

TABLE 3

|  | TiO$_2$ (anatase, Aldrich) | Example 2 | Example 3 | Example 4 |
|---|---|---|---|---|
| A/A$_{ref}$ | 0.98 | 0.34 | 0.28 | 0.34 |

Thus, it is observed that degradation of Orange G dye was made possible by the materials of examples 2 to 4, whereas TiO$_2$ (anatase, Aldrich) does not make it possible.

The degradation test on Orange II dye was carried out for the material of example 3 and the Degussa P25 TiO$_2$ (respectively FIGS. 5 and 6) under two different illumination conditions: under solar radiation and in darkness. The change in the solution containing the material was monitored for approximately 8 hours (see FIG. 5).

Figure 5:
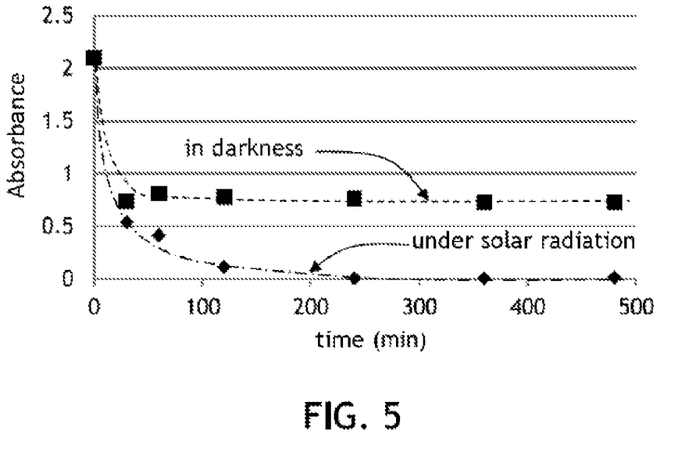
FIG. 5 is a graph representing the absorbance of the solutions containing an Orange II dye into which the material of example 3 has been added, after exposure to sun radiation and in darkness, as a function of the time between 0 and 500 min.

It can be observed, from the graph of FIG. 5, that the solution which contained the material of example 3 is completely transparent after exposure to sunlight for 250 min, in contrast to the solution which contained the same material after being placed in darkness.

Figure 6:
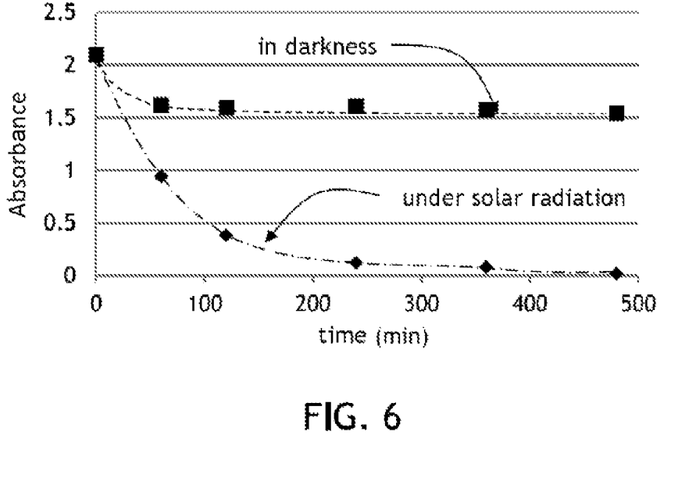
FIG. 6 is a graph representing the absorbance of the solutions containing an Orange II dye into which Degussa P25 $TiO_2$ has been added, after exposure to sun radiation and in darkness, as a function of the time between 0 and 500 min.

Furthermore, it is observed, from FIG. 6, that, although the solution which contained the Degussa P25 TiO$_2$ becomes completely transparent at the end of the test, i.e. after exposure to sunlight for more than 500 min, this result is obtained later than for the material of example 3.

The embodiments above are intended to be illustrative and not limiting. Additional embodiments may be within the claims. Although the present invention has been described with reference to particular embodiments, workers skilled in the art will recognize that changes may be made in form and detail without departing from the spirit and scope of the invention.

Various modifications to the invention may be apparent to one of skill in the art upon reading this disclosure. For example, persons of ordinary skill in the relevant art will recognize that the various features described for the different embodiments of the invention can be suitably combined, un-combined, and re-combined with other features, alone, or in different combinations, within the spirit of the invention. Likewise, the various features described above should all be regarded as example embodiments, rather than limitations to the scope or spirit of the invention. Therefore, the above is not contemplated to limit the scope of the present invention.

The invention claimed is:

1. A method for the production of a TiO$_2$ material comprising: preliminary mixing a titanium alkoxide with an acid;
    adding water, a phase separator and an N source to the mixture of titanium alkoxide and acid, thereby obtaining a TiO$_2$ gel;
    washing the TiO$_2$ gel with isopropanol (iPrOH);
    drying and calcining the TiO$_2$ gel to produce the TiO$_2$ material exhibiting open mesopores and macropores, the mesoporous volume being greater than 0.1 cm$^3$/g and the macroporous volume being greater than approximately 0.3 cm$^3$/g, the TiO$_2$ material comprising at least 60 wt. % TiO$_2$ in the form of anatase and elemental carbon and/or element nitrogen in a quantity lower or equal to approximately 2%, the percentages being calculated with respect to the total weight of the material.

2. The method of claim 1, wherein the titanium alkoxide is Ti(OiPr)$_4$.

3. The method of claim 1, wherein the titanium alkoxide: acid molar ratio is between 1:1 and 1:0.5.

4. The method of claim 1, wherein the acid is HCl.

5. The method of claim 1, wherein the phase separator is poly(ethylene oxide) (PEO) having a number average molar mass (Mn) of greater than or equal to 10 000.

6. The method of claim 1, wherein the titanium alkoxide:N source molar ratio is between 1:1 and 1:0.75.

7. The method of claim 1, wherein the N source is N-methylformamide (NFA).

* * * * *